US012733896B2

(12) United States Patent
Kim et al.

(10) Patent No.: US 12,733,896 B2
(45) Date of Patent: Sep. 15, 2026

(54) DIGESTIVE CANAL SCANNING DEVICE, BODY SCANNING DEVICE, BODY SCANNING METHOD AND ACOUSTIC-BASED DIGESTIVE ORGAN MONITORING SYSTEM

(71) Applicant: KOREA UNIVERSITY RESEARCH AND BUSINESS FOUNDATION, Seoul (KR)

(72) Inventors: Eun-sun Kim, Seoul (KR); Seung-Jong Kim, Seoul (KR); Yongdoo Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1296 days.

(21) Appl. No.: 17/601,247

(22) PCT Filed: Apr. 2, 2020

(86) PCT No.: PCT/KR2020/004531
§ 371 (c)(1),
(2) Date: May 10, 2022

(87) PCT Pub. No.: WO2020/204639
PCT Pub. Date: Oct. 8, 2020

(65) Prior Publication Data

US 2022/0296204 A1 Sep. 22, 2022

(30) Foreign Application Priority Data

Apr. 5, 2019 (KR) ........................ 10-2019-0040140
Apr. 29, 2019 (KR) ........................ 10-2019-0049913
May 9, 2019 (KR) ........................ 10-2019-0054324

(51) Int. Cl.
*A61B 7/00* (2006.01)
*A61B 5/00* (2006.01)
(Continued)

(52) U.S. Cl.
CPC ............ *A61B 7/008* (2013.01); *A61B 5/4255* (2013.01); *A61B 5/6823* (2013.01); *A61B 7/04* (2013.01);
(Continued)

(58) Field of Classification Search
CPC ..... A61B 7/008; A61B 5/4255; A61B 5/6823; A61B 7/04; A61B 2562/0204; A61B 5/061
See application file for complete search history.

(56) References Cited

U.S. PATENT DOCUMENTS

2011/0040203 A1 2/2011 Savage
2017/0056451 A1* 3/2017 Meron .................. A61B 7/008
2017/0367642 A1 12/2017 Meron

FOREIGN PATENT DOCUMENTS

CN 102008316 4/2011
CN 104305961 1/2015
(Continued)

*Primary Examiner* — May A Abouelela
*Assistant Examiner* — Yasmeen S Warsi
(74) *Attorney, Agent, or Firm* — DUANE MORRIS LLP; Gregory M. Lefkowitz; Brandon A. Chan

(57) ABSTRACT

A digestive canal scanning device of the present invention includes a sensor module, a data processing unit, and an analysis unit. A body scanning device of the present invention includes a sensor module, a data processing unit, and an analysis unit. An acoustic digestive organ monitoring system of the present invention includes an auscultation unit, an artifact collection unit, a signal extraction unit, a feature extraction unit, a database, an artificial neural network, and a wireless communication unit.

9 Claims, 13 Drawing Sheets

(51) Int. Cl.
*A61B 7/04* (2006.01)
*G06F 17/14* (2006.01)

(52) U.S. Cl.
CPC .... *G06F 17/142* (2013.01); *A61B 2562/0204* (2013.01)

(56) References Cited

FOREIGN PATENT DOCUMENTS

| | | |
|---|---|---|
| CN | 106328150 | 1/2017 |
| CN | 108175436 | 6/2018 |
| CN | 108514428 | 9/2018 |
| JP | 2000-262523 | 9/2000 |
| KR | 101407049 | 6/2014 |
| KR | 1020150007738 | 1/2015 |
| KR | 101870121 | 6/2018 |

* cited by examiner

DIGESTIVE CANAL SCANNING DEVICE, BODY SCANNING DEVICE, BODY SCANNING METHOD AND ACOUSTIC-BASED DIGESTIVE ORGAN MONITORING SYSTEM

CROSS-REFERENCE TO RELATED APPLICATIONS

This application is a § 371 national stage entry of International Application No. PCT/KR2020/004531, filed on Apr. 2, 2020, which claims priority to Korean Patent Application No. 10-2019-0040140 filed on Apr. 5, 2019, Korean Patent Application No. 10-2019-0049913 filed on Apr. 29, 2019, and Korean Patent Application No. 10-2019-0054324 filed on May 9, 2019, the entire contents of which are incorporated herein by reference.

TECHNICAL FIELD

The present invention relates to a digestive canal scanning device that can locate intestinal stenosis or intestinal adhesion based on sound from the digestive canal.

The present invention also relates to a body scanning device that can extract a sound exhibiting a medical problem to locate the sound in a patient body by scanning internal organs of the patient body, such as the chest or the digestive canal, through detection of sounds in an audible or inaudible band from the patient body, followed by analyzing a frequency spectrum of the sound in the patient body through an artificial intelligence (AI) algorithm, and a body scanning method thereof.

The present invention also relates to an acoustic digestive organ monitoring system that enables early diagnosis of disease in the digestive system of a patient by continuously monitoring the digestive system through establishment of a database based on biological sounds generated from the digestive system.

BACKGROUND ART

As a part of the human digestive organs, the large intestine has a length of about 1.5 m, whereas the small intestine is a very long organ having a length of about 6 m to 7 m. Thus, the small intestine can suffer intestinal stenosis in which the canal narrows or intestinal adhesion in which the canal sticks together. Intestinal stenosis or adhesion can provide other serious problems through intestinal perforation or intestinal obstruction, thereby causing an emergency situation that requires treatment, such as surgery and the like, as needed.

Since even a patient undergoing intestinal stenosis may not continuously feel pain, it is not easy for a doctor to diagnose intestinal stenosis or adhesion through location of intestinal stenosis with a stethoscope and the like. Although an improved method, such as computed tomography (CT) and magnetic resonance imaging (MRI), can be used, difficulty in location of intestinal stenosis often results in repeated imaging, causing overtreatment problems.

On the other hand, there are several types of surgical procedures performed in hospitals and one of the surgical procedures is open surgery performed by opening the abdomen of a patient. For example, when a part of the stomach is resected for gastric cancer treatment, the surgery is performed after opening the patient abdomen. After gastric resection, the internal organs are rearranged and the abdomen is stitched again to complete the surgery. Since the small intestine has a length of about 6 m to 7 m, the abdomen can be stitched with a part of the small intestine twisted or bent even when the internal organs are rearranged well. In some patients with very severe intestinal twists or bends, food cannot proceed past the corresponding region in the intestine, causing perforation of the intestine when this condition is kept for a certain period of time or more. If perforation occurs in the intestine, it is necessary to perform reoperation. Perforation of the intestine can occur together with intestinal adhesion and repetition of operation increases the possibility of intestinal adhesion.

If it is possible to previously check that there is such a problem in the small intestine of a patient after surgery, laparoscopic surgery or other relatively low-risk methods can be used without performing open surgery again. However, currently, there is no easy way to locate a twisted or bent portion of the small intestine, as in diagnosis of intestinal stenosis or intestinal adhesion. As described above, it is often difficult to locate the twisted or bent portion of the small intestine with a stethoscope and it is also difficult to find intestinal stenosis and perforation even through computed tomography or magnetic resonance imaging. Even with endoscopy, a doctor can see the internal organs from the neck to the stomach and from the rectum to the large intestine, and cannot see the small intestine.

DETAILED DESCRIPTION OF THE INVENTION

Problems to be Solved by the Invention

It is an object of the present invention to provide a digestive canal scanning device that can locate intestinal stenosis or intestinal adhesion through diagnosis of intestinal stenosis or intestinal adhesion based on a sound from the digestive canal of a patient by scanning the digestive canal through detection of sounds in the patient abdomen.

It is another object of the present invention to provide a body scanning device that can extract a sound with a medical problem to locate the sound in a patient body by scanning internal organs of the patient body, such as the chest or the digestive canal, through detection of sounds in an audible or inaudible band from the patient body, followed by analyzing a frequency spectrum of the sound in the patient body with an artificial intelligence (AI) algorithm, and a body scanning method thereof.

It is a further object of the present invention to provide an acoustic digestive organ monitoring system that enables early diagnosis of disease in the digestive system of a patient by continuously monitoring the digestive system through establishment of a database based on biological sounds generated from the digestive system.

Means for Solving the Problems

In accordance with one aspect of the present invention, a digestive canal scanning device includes a sensor module, a data processing unit, and an analysis unit to locate a part of the digestive canal of a patient generating a digestive canal sound. The sensor module includes multiple microphones attached to multiple sites separated from each other on the patient abdomen and detecting sounds from the abdomen after the patient swallows food. The data processing unit converts analog signals generated from the multiple microphones into digital audio signals. The analysis unit may classify the digestive canal sound among multiple audio signals converted by the data processing unit and may recognize that a location of a microphone detecting a signal classified as the digestive canal sound is a location at which the digestive canal sound is generated.

According to one embodiment, the sensor module may include multiple unidirectional microphones; and an attachment pad attached to the patient abdomen and receiving the multiple microphones to be separated from each other. The multiple microphones may include at least two microphones separated from each other by a distance enabling detection of the same digestive canal sound.

According to one embodiment, the digestive canal scanning device may further include a soundproof pad coupled to an inner surface of the attachment pad.

According to one embodiment, the digestive canal scanning device may further include a display unit displaying a two-dimensional lattice map. The multiple microphones may be disposed at locations corresponding to intersection points of the lattice map and the analysis unit may visually mark the location of the microphone detecting the digestive canal sound on the two-dimensional lattice map.

According to another embodiment, the digestive canal scanning device may further include multiple marking lamps attached to the multiple microphones, respectively; and a drive unit turning on a marking lamp attached to the microphone detecting the digestive canal sound among the multiple marking lamps under control of the analysis unit.

According to another embodiment, the digestive canal scanning device may further include a speaker outputting the detected digestive canal sound under control of the analysis unit.

Classification of the digestive canal sound by the analysis unit may be performed by various algorithms. In one embodiment, the analysis unit may compare locations at which multiple audio signals are generated with each other, followed by treating an audio sound generated from a location separated a preset distance from other locations, at which audio signal are generated, as noise. In another embodiment, the analysis unit may be provided with characteristic data exclusive to the digestive canal sound to classify an audio signal having the same characteristics as the characteristic data as the digestive canal sound through spectrum analysis of each of the multiple audio signals. Here, the characteristic data may be a combination of frequencies unique to the digestive canal sound.

A body scanning device according to the present invention proposes a method of collecting internal body sounds in a patient body through multiple microphones by focusing on the fact that some of the internal body sounds can be important means for clinically diagnosing patient disease. In particular, the body scanning device according to the present invention proposes a method of tracing a corresponding location through classification and analysis of a sound generated when the internal organs of the patient have a medical problem (hereinafter referred to as "sound of interest") among the internal body sounds using an artificial intelligence engine or algorithm that learns frequency characteristics of the sound of interest and a pattern of collecting the internal body sounds by the multiple microphones.

In accordance with another aspect of the present invention, a body scanning device includes: a sensor module, a data processing unit, and an analysis unit to locate a part of a patient body generating an internal body sound. The sensor module includes multiple microphones attached to the patient body to be separated from each other and detecting an internal body sound generated from the patient body. The data processing unit converts audio signals generated from the multiple microphones into digital signals to obtain frequency information of the audio signals through fast Fourier transform. The analysis unit may classify the internal body sound generated from the patient body among multiple audio signals generated from the multiple microphones based on the frequency information provided by the data processing unit and may recognize that a location of a microphone detecting the internal body sound is a location at which the internal body sound is generated.

According to one embodiment, the analysis unit may learn frequency characteristics of a sound generated from the patient internal organs in a preset state through artificial intelligence to detect an audio signal having the frequency characteristics among audio signals classified as the internal body sound. Here, the analysis unit may obtain the preset frequency characteristics by learning frequency characteristics of the internal body sound based on frequency information obtained through fast Fourier transform of the multiple audio signals provided as learning data.

According to one embodiment, the analysis unit may locate a part of the patient body generating the internal body sound through analysis of a pattern of collecting the same internal body sounds between the multiple microphones using artificial intelligence.

According to one embodiment, the sensor module may include multiple unidirectional microphones; and an attachment pad attached to the patient abdomen and receiving the multiple microphones to be separated from each other. The multiple microphones may include at least 8 microphones separated from each other by a distance enabling detection of the same internal body sound.

According to one embodiment, the body scanning device may further include a display unit displaying a two-dimensional lattice map. Here, the multiple microphones may be disposed at locations corresponding to intersection points of the lattice map and the analysis unit may visually mark the location of the microphone detecting the internal body sound on the two-dimensional lattice map.

According to another embodiment, the body scanning device may further include multiple marking lamps attached to the multiple microphones, respectively; and a drive unit turning on a marking lamp attached to the microphone detecting the internal body sound among the multiple marking lamps under control of the analysis unit.

According to another embodiment, the body scanning device may further include a speaker outputting the detected internal body sound under control of the analysis unit.

Classification of the internal body sound by the analysis unit may be performed by various algorithms. In one embodiment, the analysis unit may compare locations at which multiple audio signals are generated with each other, followed by treating an audio sound generated from a location separated a preset distance from locations at which other audio signals are generated, as noise. In another embodiment, the analysis unit may be provided with characteristic data unique to the internal body sound to classify an audio signal having the same characteristics as the characteristic data as the internal body sound through spectrum analysis of each of the multiple audio signals. Here, the characteristic data may be combination of frequencies unique to the internal body sound.

In accordance with a further aspect of the present invention, a body scanning method may include: attaching multiple microphones to a scanning target region on a patient body to be separated from each other on the patient body, followed by collecting internal body sounds of the patient body; converting, by a data processing unit, audio signals collected by the multiple microphones into digital signals to obtain frequency information of the audio signals through fast Fourier transform of the audio signals; classifying, by an analysis unit, an internal body sound among the audio signals generated from the multiple microphones using the frequency information to recognize that a location of a microphone detecting the internal body sound is a location at which the internal body sound is generated.

In accordance with yet another aspect of the present invention, an acoustic digestive organ monitoring system includes: multiple auscultation units attached to various locations on a patient abdomen to collect a biological sound group generated from the patient digestive system; at least one artifact collection unit attached to the patient abdomen to collect an artifact group generated outside the patient; a signal extraction unit comparing the biological sound group collected by the auscultation unit with the artifact group collected by the artifact collection unit to filter noise from the biological sound group after removing the artifact group from the biological sound group; a feature extraction unit extracting the biological sound group into multiple biological sound sources through division of the biological sound group, from which the artifact group is removed by the signal extraction unit, using spatial features of the patient digestive system; a database to which the biological sources extracted by the feature extraction unit are input; an artificial neural network monitoring the biological sources input to the database to output a biological sound target corresponding to a digestive system disease as a diagnosis result among the biological sound sources input to the database; and a wireless communication unit sending the diagnosis result to a control server.

In addition, the acoustic digestive organ monitoring system may further include multiple visceral electromyography (EMG) collecting units each collecting motion potentials of visceral muscles generated in the patient internal organs as a visceral EMG group and transmitting the visceral EMG group to the feature extraction unit.

Effects of the Invention

The digestive canal scanning device according to the present invention can recognize and mark a location of intestinal stenosis or intestinal adhesion through diagnosis of intestinal stenosis or intestinal adhesion based on an internal body sound of a patient through detection of sounds in the patient abdomen.

The digestive canal scanning device according to the present invention can easily determine intestinal stenosis or adhesion by marking a location of sounds generated from the digestive canal of a patient due to food taken by the patient on a two-dimensional map.

The digestive canal scanning device according to the present invention enables diagnosis of intestinal stenosis or adhesion and location of intestinal stenosis or adhesion in the patient body while preventing the patient from feeling pain continuously. Accordingly, even when it is difficult to diagnose intestinal stenosis and the like with a stethoscope depending upon patient conditions, the digestive canal scanning device according to the present invention enables easy diagnosis of intestinal stenosis and the like and does not cause overtreatment problems through repetition of computed tomography (CT) or magnetic resonance imaging (MRI) for diagnosis of intestinal stenosis and the like.

In particular, the digestive canal scanning device according to the present invention is used after open surgery, thereby preventing intestinal stenosis or adhesion from progressing to intestinal perforation or intestinal obstruction in an early stage while a patient does not feel pain.

The body scanning device according to the present invention can assist in clinical diagnosis of patient disease by detecting not only sounds in audible and inaudible bands generated inside the patient body (abdomen, lungs, bronchial tubes, etc.), but also a sound (sound of interest) generated when the patient internal organs are in a medically problematic condition.

The body scanning device according to the present invention can trace internal body sounds through multiple microphones attached to the patient body while minimizing errors using artificial intelligence that has learned the sound of interest and can achieve more accurate location of the sound of interest through artificial intelligence that has learned a pattern of collecting the internal body sounds by the multiple microphones.

The body scanning device according to the present invention can collect and analyze sounds in the audible and inaudible bands, thereby enabling easy tracing of diseases in an early stage, which are difficult to detect when a doctor directly analyzes images presented by conventional body scanning devices, such as computed tomography (CT) or magnetic resonance imaging (MRI).

The acoustic digestive organ monitoring system according to the present invention enables early diagnosis of disease in the digestive system of a patient by continuously monitoring the patient digestive system through establishment of a database based on biological sounds generated from the patient's digestive system.

MODE FOR CARRYING OUT THE INVENTION

Hereinafter, exemplary embodiments of the present invention will be described in detail with reference to the accompanying drawings.

Figure 1:
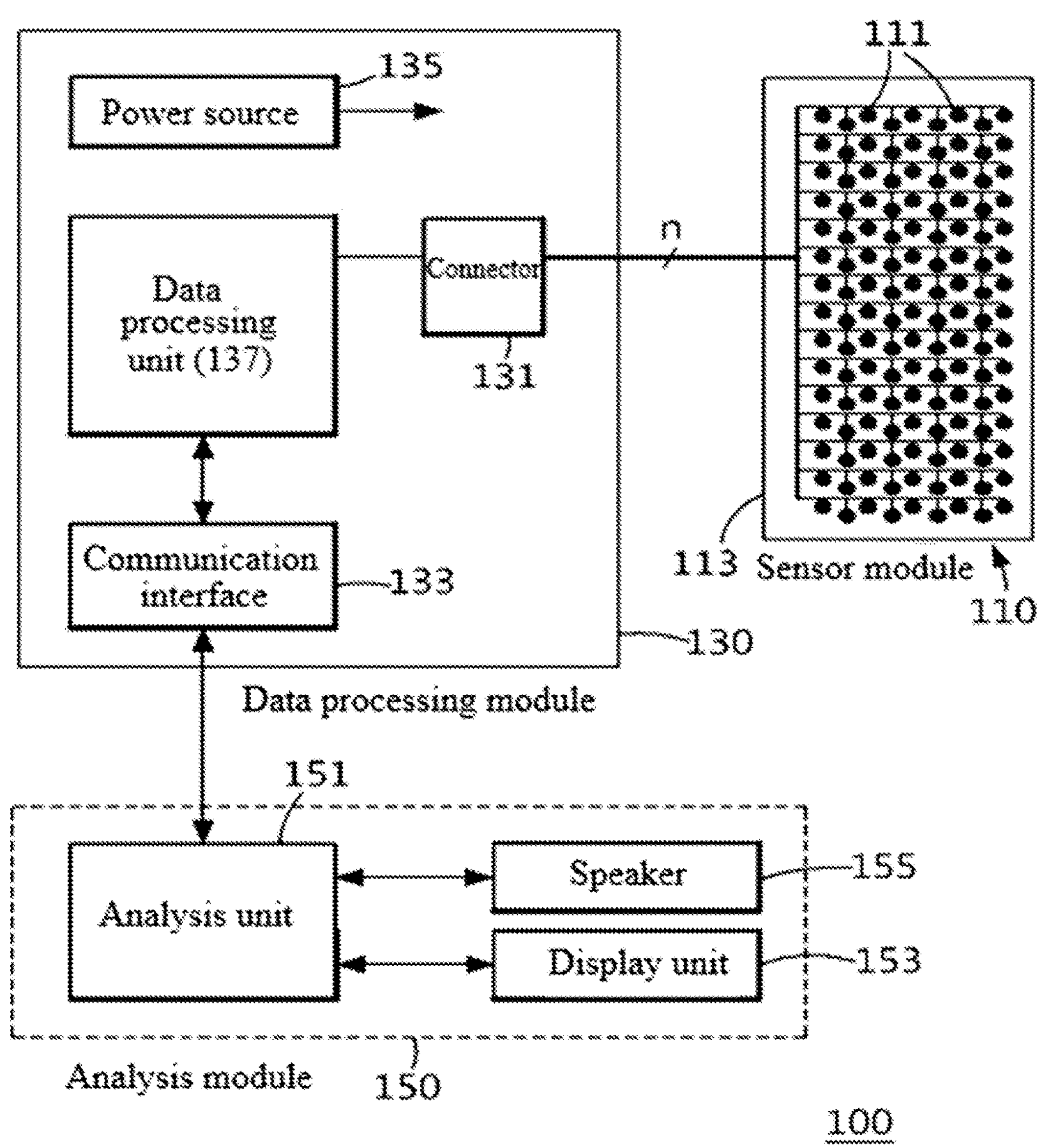
FIG. 1 is a block diagram of a digestive canal scanning device according to the present invention.
Figure 2:
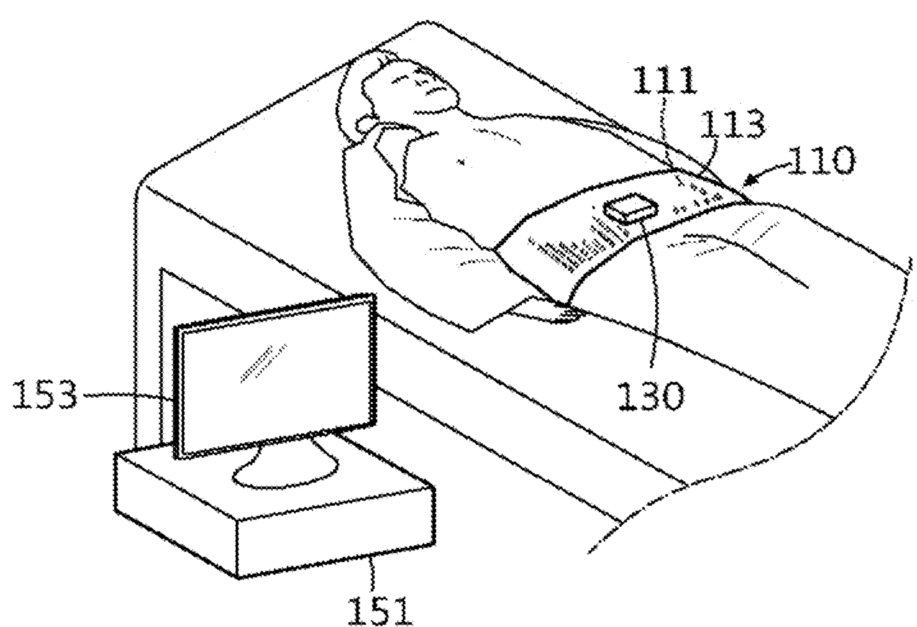
FIG. 2 is a view of the digestive canal scanning device according to the present invention.

Referring to FIG. 1 and FIG. 2, a digestive canal scanning device 100 according to the present invention includes a sensor module 110 attached to the abdomen of a patient, a data processing module 130, and an analysis module 150 to locate a "sound generated from the digestive canal" of the patient (hereinafter, "digestive canal sound"). The data processing module 130 may be realized by a separate component from the sensor module 110 attached to the patient abdomen or may be integrally formed therewith, as shown in FIG. 2. In another embodiment, the data processing module 130 and the analysis module 150 may be realized by one device such as a kiosk and the sensor module 110 may be connected to the kiosk.

The sensor module 110 includes multiple microphones 111 attached to the patient abdomen, an attachment pad 113 receiving the multiple microphones 111, and a soundproof pad (not shown) for sound collection. The sensor module 110 receives operation power supplied from the data processing module 130 and analog audio signals obtained by the multiple microphones 111 are supplied to the data processing module 130.

First, the attachment pad 113 receives the multiple microphones 111 to be separated from each other and is attached to the patient abdomen. Accordingly, the attachment pad 113 may be formed of a deformable material, such as a synthetic resin, fibers, a silicone resin, and the like. As shown in FIG. 2, the attachment pad 113 may be realized by a single pad capable of receiving all of the microphones 111 or may be realized by three or four pads separated from each other and each receiving the microphones 111.

The soundproof pad serves to collect sounds generated from the patient abdomen. Accordingly, the soundproof pad has a cylindrical shape and is coupled to an inner surface of the attachment pad 113 with a central axis of the cylindrical shape disposed coincident with a central axis of the attachment pad 113. In addition, the soundproof pad may be formed with multiple grooves (not shown) on an outer surface thereof to secure soundproofing against external noise.

According to the present invention, since the location of the microphone 111 recognizing a digestive canal sound is treated as a location at which the digestive canal sound is generated, the microphones 111 may be unidirectional microphones having good sensitivity to sound in one direction and may have as narrow a sound receiving region as possible. In consideration of the sensor module 110 attached to the patient abdomen, the microphones 111 may be arranged to detect sounds in a perpendicular direction to the attachment pad 113. Furthermore, in order to prevent external noise from being collected by the microphones 111 as much as possible, the microphones 111 may be received in the attachment pad 113 such that a sound collecting surface of each microphone 111 can be attached to the abdomen.

Figure 3:
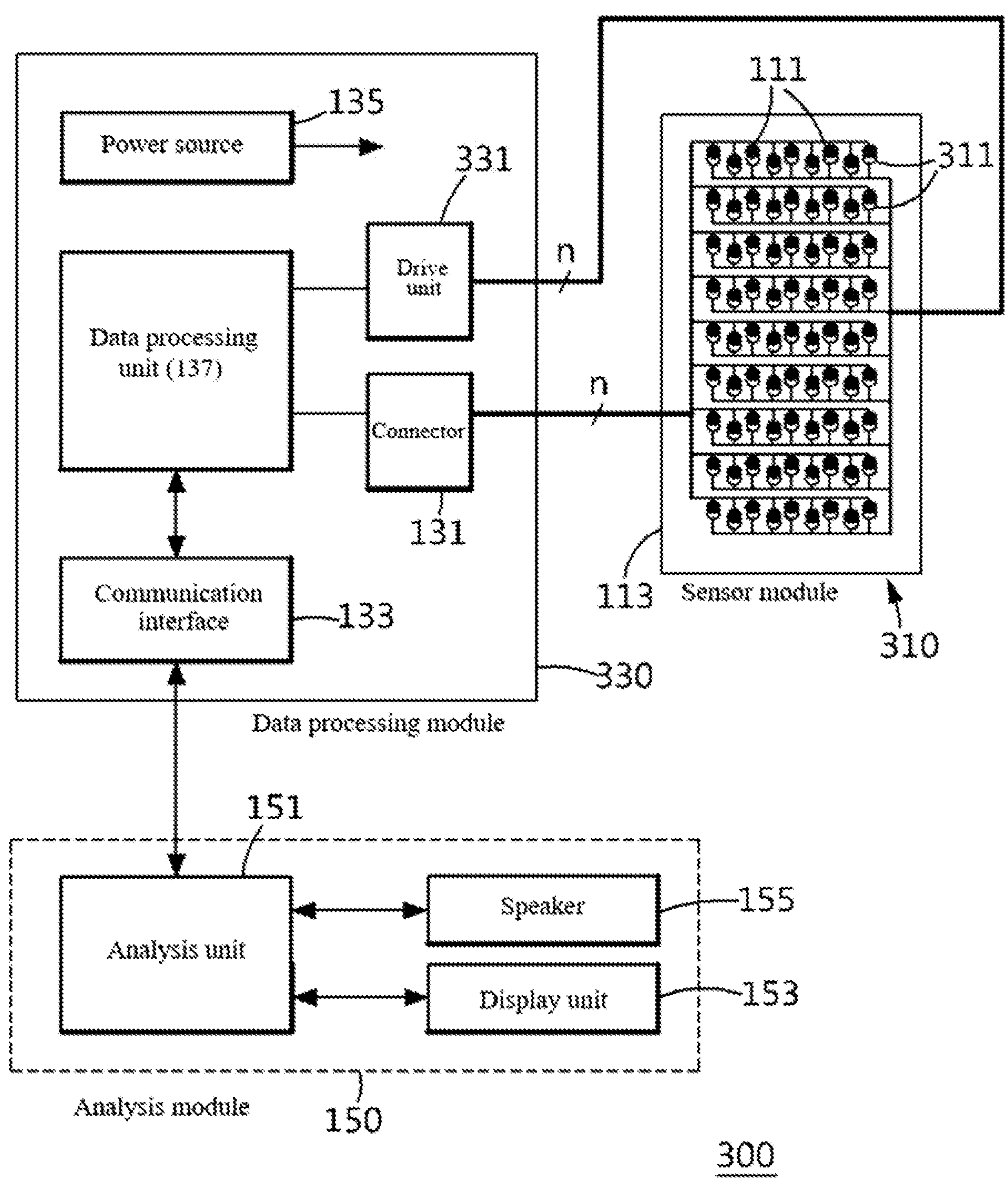
FIG. 3 is a block diagram of a digestive canal scanning device according to another embodiment of the present invention.

The multiple microphones 111 received in the attachment pad 113 may be attached to or brought into close contact with multiple sites separated from each other in an abdominal region of the patient (or in an intestinal region narrower than the abdominal region). Since the scanning device 100 according to the present invention is adapted to diagnose intestinal stenosis or intestinal adhesion, the microphones 111 are generally disposed in consideration of the thickness of the small intestine and a general location of the small intestine in the abdomen. Since the small intestine is a relatively narrow and fairly long digestive canal that remains clumped rather than stretched out, the microphones 111 may be disposed in a denser arrangement. It is desirable that the microphones 111 be arranged at an interval that allows at least two microphones 111 to detect a digestive canal sound generated from one site. In consideration of these circumstances, the sensor module 110 may be provided with dozens of microphones 111. Referring to FIG. 1 and FIG. 3, by way of example, the multiple microphones 111 are arranged at constant intervals in a two-dimensional matrix so as to cover the abdomen (or a small intestinal region) of the patient. It should be understood that the multiple microphones 111 may be arranged at different intervals depending on arrangement of the small intestine obtained through experiments or statistics.

The sensor module 110 detects the sounds generated from the abdomen and supplies data of the sounds to the data processing module 130. According to a method of using the scanning device 100 according to the present invention, the sensor module 110 detects a digestive canal sound produced by the patient when food (or digested food) passes through the digestive canal after the patient has swallowed the food for diagnosis of intestinal stenosis. Although the sensor module 110 is attached to the patient abdomen and each of the microphones 111 is unidirectional, external noise other than abdominal sounds can be collected together with sounds from organs other than the digestive canal.

The data processing module 130 supplies operation power to the sensor module 110 and converts the digestive canal sound detected by the sensor module 110 into digital signals to supply the digital signals to the analysis module 150. To this end, the data processing module 130 includes a connector 131, a communication interface 133, a power source 135, and a data processing unit 137.

The power source 135 supplies operation power not only to the data processing module 130 but also to the sensor module 110. For power supply to the multiple microphones 111, an output terminal of the power source 135 is directly connected to each of the microphones 111 through series and/or parallel connection. In the embodiment shown in FIG. 3 described below, the power source 135 may also supply electric power for turning on marking lamps 311.

The connector 131 supplies the analog audio signals collected by the multiple microphones 111 to the data processing unit 137. The analog audio signals collected by the multiple microphones 111 are supplied to the data processing unit 137 through individual channels to be distinguished from each other. However, since it is difficult for a general data processing unit 137 to have several dozen channels (or input terminals), the connector 131 supplies the analog audio signals collected by the multiple microphones 111 to the data processing unit 137 after muxing the analog audio signals. Accordingly, the data processing unit 137 including several dozen channels (or input terminals) may omit the connector 131.

The communication interface 133 is a communication means for connection between the data processing unit 137 and an analysis unit 151 and is used when the data processing module 130 is realized as a separate device from the analysis unit 151. Accordingly, the communication interface 133 is not essential to the present invention and may be omitted when the data processing module 130 is integrally formed with the analysis unit 151. The communication interface 133 may be a wired interface or may be a wireless interface as shown in FIG. 2.

The data processing unit 137 converts the audio signal of each channel input through the connector 131 into a digital signal to supply the digital signal to the analysis unit 151. The data processing unit 137 may perform fundamental noise filtering to remove white noise or noise less than a predetermined level.

Referring to FIG. 1 and FIG. 3, the analysis module 150 is separated from the data processing module 130 and is connected thereto through a communication channel. Alternatively, the analysis module 150 may be integrally formed with the data processing module 130, as described above.

The analysis module 150 may locate the digestive canal sound based on the digital audio signal sent from the data processing module 130 and may mark a location at which the digestive canal sound is generated. To this end, the analysis module 150 includes the analysis unit 151 and the display unit 153. Next, operation of the analysis unit 151 according to the present invention will be described with reference to FIG. 1 to FIG. 5.

<Sound Collection: S501>

The sensor module 110 collects sounds generated from the abdomen of a patient through the multiple microphones 111 and the data processing unit 137 converts audio signals supplied through the multiple channels into digital signals to supply the digital signals to the analysis unit 151.

<Classification and Location of Digestive Canal Sound: S503, S505>

The analysis unit 151 classifies a digestive canal sound among digital audio signals supplied from the data processing unit 137 through multiple channels. The sounds collected by the sensor module 110 may include not only the digestive canal sound but also various types of noise. In some cases, only noise can be collected without the digestive canal sound.

Detailed classification of the digestive canal sound by the analysis unit 151 may be realized by various algorithms. For example, (1) the analysis unit 151 may classify all sounds having a predetermined level or more into the digestive canal sound. Since the digestive canal scanning device 100 according to the present invention is an assistant device for diagnosis of intestinal stenosis or intestinal adhesion and final diagnosis relies on doctors or medical professionals, it may be necessary to recognize and mark the location of all sounds having a predetermined level or more.

(2) In another example, the analysis unit 151 may be provided with characteristic data exclusive to the digestive canal sound. Here, the "characteristic data" may be combination of frequencies unique to the digestive canal sound and may be obtained through experiments. The analysis unit 151 may classify an audio signal having the same characteristics as the characteristic data as the digestive canal sound through spectrum analysis of each of the multiple audio signals supplied through multiple channels and may classify an audio signal not having the same characteristics as the characteristic data as noise.

(3) On the other hand, since the small intestine is a single connected canal regardless of an arrangement shape of the small intestine in the patient abdomen, sounds generated from the abdomen are captured as a stream by the multiple microphones 111 arranged in a matrix or in an array. Accordingly, a digestive canal sound not included in a series of streams may be classified as noise. For example, in comparison of locations at which multiple audio signals are generated with each other, an audio signal generated from a location separated a predetermined distance from locations at which other audio signals are generated may be treated as noise.

When there is a digestive canal sound among the audio signals supplied from the data processing unit 137 through the multiple channels, the analysis unit 151 may recognize a location at which a signal classified as the corresponding digestive canal sound is collected, (that is, a location of the corresponding microphone), as a location at which the digestive canal sound is generated.

<Marking Location of Digestive Canal Sound: S507>

The analysis unit 151 may inform a manager or a patient of the location at which the audio signal classified as the digestive canal sound is collected by marking the location. Here, the analysis module 150 may mark the location in various ways. First, the analysis unit 151 marks the location at which the digestive canal sound is generated. By tracing the digestive canal sound after the patient has swallowed food, it is possible to trace a region of the digestive canal through which the food is passing. If there are regions in which intestinal stenosis or intestinal adhesion occurs, it is marked that movement of the food is no longer progressing. Accordingly, if the digestive canal sound progresses and then stops, a doctor can suspect that intestinal twisting, intestinal bending, intestinal stenosis, or intestinal adhesion occurs in the corresponding region. Therefore, the analysis module 150 marks the location where the signal classified as the digestive canal sound is collected, that is, the location where the digestive canal sound is generated.

Figure 4:
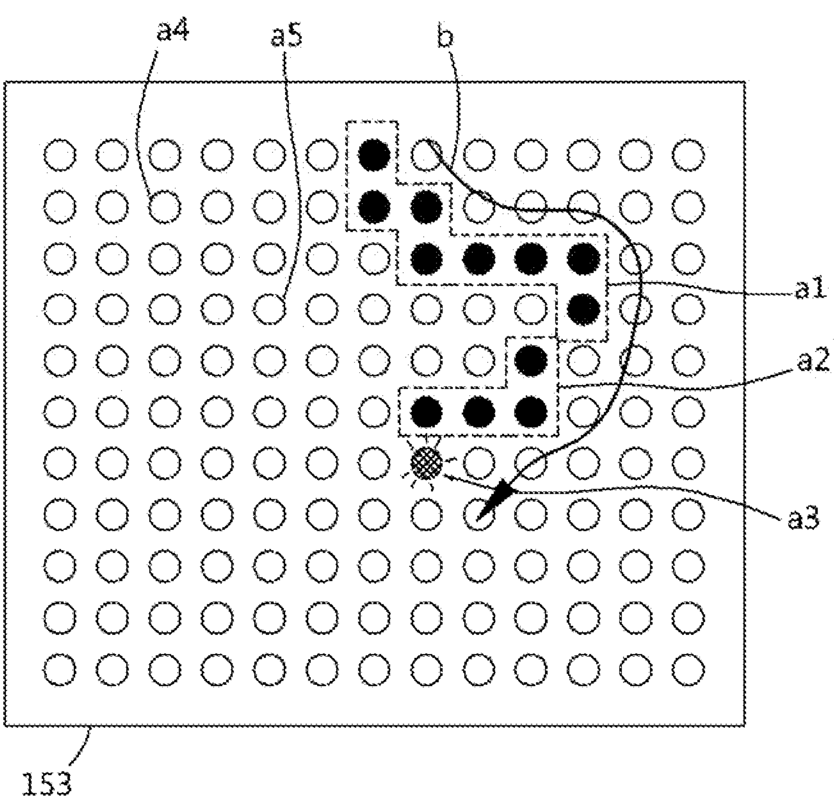
FIG. 4 is a view of one example of a digestive canal sound detection map displayed on a display unit.
Figure 5:
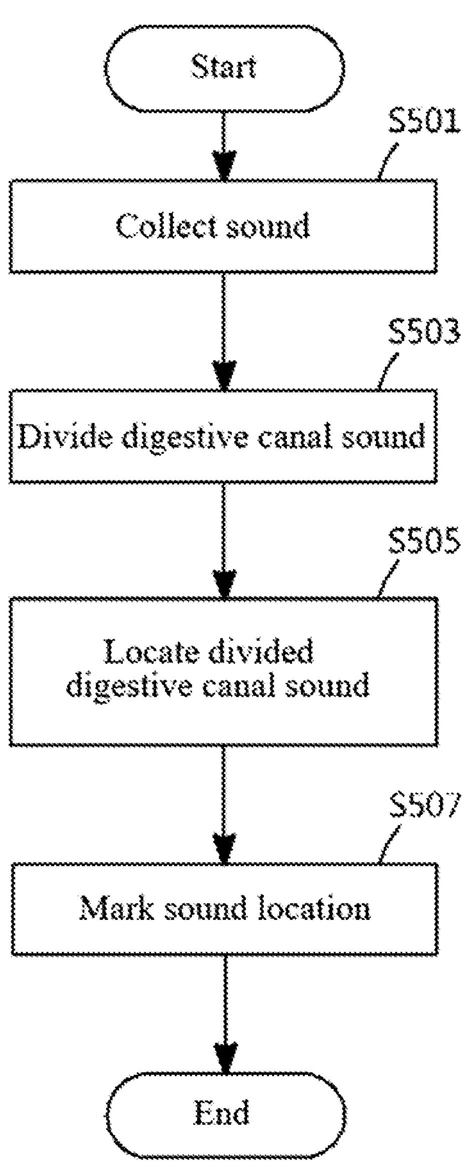
FIG. 5 is a flowchart illustrating operation of the digestive canal scanning device according to the present invention.

To this end, as shown in FIG. 1 and FIG. 3, the analysis module 150 may be provided with a display unit 153. The display unit 153 is a typical display device, such as a liquid crystal display (LCD), a light emitting diode (LED) display, an organic light emitting diode (OLED) display, a Braun tube, and the like. The analysis unit 151 may display a matrix map or a lattice map on the display unit 153, as shown in FIG. 4. Marks a1, a2, a3, a4, a5 corresponding to the multiple microphones 111 of the sensor module 110 are marked at intersection points on the matrix map. The analysis unit 151 marks the locations of the microphones 111 detecting the digestive canal sound on a two-dimensional lattice map. Referring to FIG. 4, twelve marks a1, a2 are marked in a turned on state and a thirteenth mark a3 is marked in a turned off state to indicate that the last digestive canal sound is obtained at the location of the thirteenth mark a3. Accordingly, the doctor can confirm that food is moving in an arrow direction. The digestive canal sound captured at another location, for example, at a4 or a5, which is not included in the series of connected flows, may be classified as noise.

FIG. 3 is a block diagram of a digestive canal scanning device 300 according to another embodiment of the present invention. The digestive canal scanning device 300 shown in FIG. 3 has the same configuration as the digestive canal scanning device 100 shown in FIG. 1 except that a sensor module 310 further includes multiple marking lamps 311 together with the multiple microphones 111 and a data processing module 330 further includes a drive unit 331 for driving the marking lamps 311. The power source 135 supplies power to the marking lamps 311.

The marking lamps 311 are attached to the multiple microphones 111 mounted on a scanning module 310, respectively. Under control of the analysis unit 151, the drive unit 331 turns on the marking lamp 311 attached to the microphone 111 that detects the digestive canal sound, whereby a current location of the digestive canal sound can be marked on the patient abdomen. Since the location marked on the display unit 153 does not indicate a particular location on the patient abdomen, the location marked on the display unit 153 may be marked on the patient abdomen by the marking lamp 311. The marking lamps 311 may be realized by LEDs or other lamps similar thereto.

The drive unit 331 is a switch block connecting the power source 135 to the multiple marking lamps 311 and individually controls supply of operation power to the multiple marking lamps 311. Here, the drive unit 331 may open a particular switch in response to a separate control signal to allow a particular marking lamp 311 to be turned on. When the analysis unit 151 recognizes the location at which the digestive canal sound is detected, the analysis unit 151 informs the drive unit 331 of the corresponding location through the data processing unit 137.

According to this embodiment, the digestive canal scanning device 300 may further include a speaker 155 that outputs the detected digestive canal sound under control of the analysis unit 151. An experienced doctor can determine whether the sound output from the speaker 155 is the digestive canal sound.

The digestive canal scanning device according to the present invention is operated by the method described above.

Figure 6:
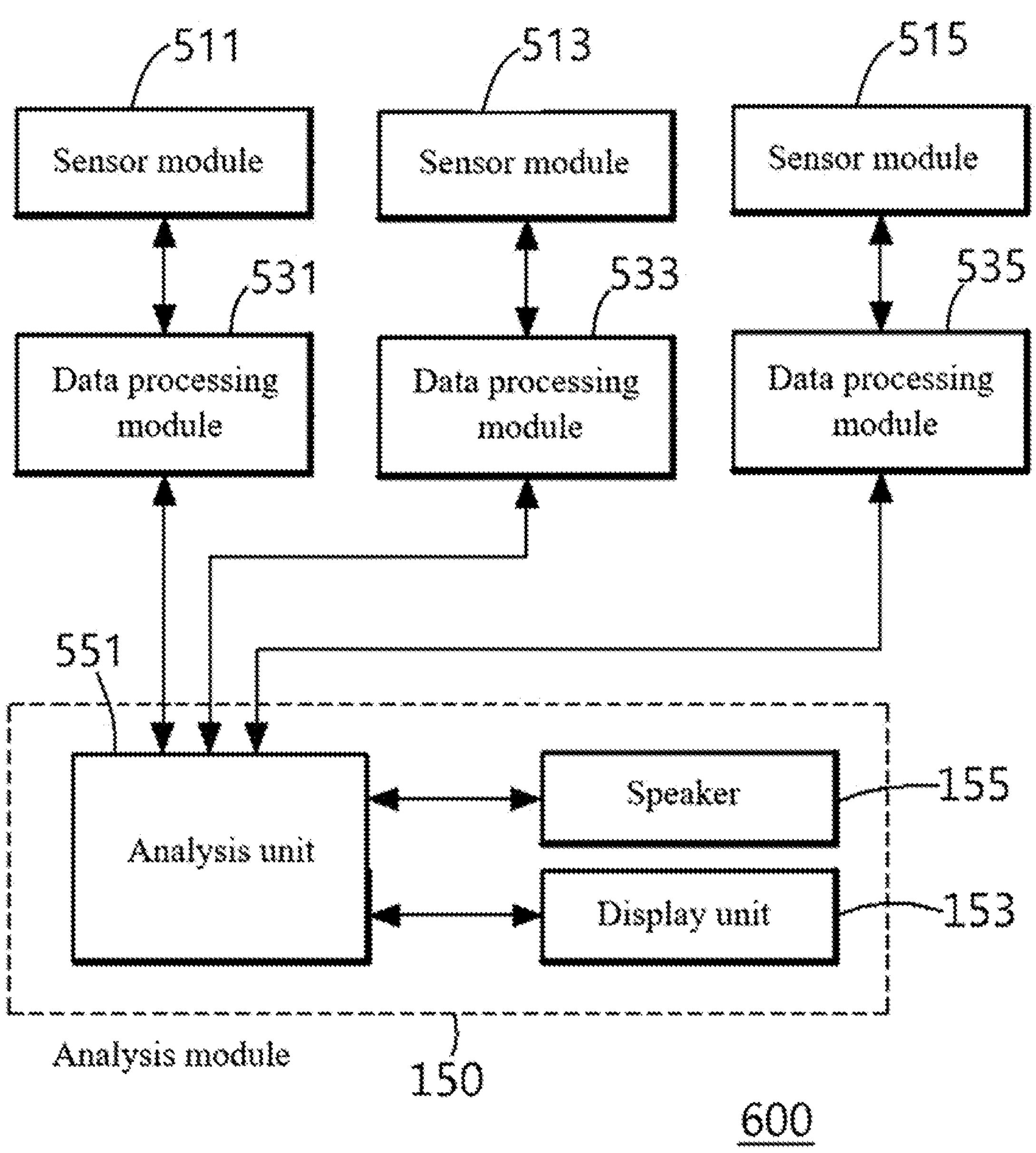
FIG. 6 is a block diagram of a digestive canal scanning device according to a further embodiment of the present invention.

FIG. 1 and FIG. 3 show one example in which one data processing module 130 and the sensor module 110 are connected to the analysis module 150. In another embodiment, multiple data processing modules may be connected to the analysis module 150. FIG. 6 shows a scanning device 600 in which an analysis module 150 is connected to multiple data processing units 531, 533, 535, which are connected to sensor modules 511, 513, 515, respectively.

The sensor modules 511, 513, 515 are one example of the sensor module 110 realized using multiple pads, as described in the embodiments of FIG. 1 and FIG. 3. Accordingly, the configuration and operation of the sensor modules are the same as the sensor module 110. In this embodiment, each of the sensor modules 511, 513, 515 includes a smaller number of microphones 111 than the sensor module 110 shown in FIG. 1 and FIG. 3.

The data processing units 531, 533, 535 distribute the role of the data processing unit 130 shown in FIG. 1 and FIG. 3. Although each of the data processing units 531, 533, 535 has the same inner configuration as the data processing unit 130, each of the data processing units 531, 533, 535 has a smaller number of treatment audio channels than the data processing unit 130. Accordingly, the data processing units 531, 533, 535 may omit the connector 131.

An analysis unit 551 is connected to the multiple data processing units 531, 533, 535 and the methods of classifying the digestive canal sound and marking the sound generating location are the same as those of the analysis unit 151 shown in FIG. 1 and FIG. 3.

Next, a body scanning device according to the present invention and a body scanning method thereof will be described.

Figure 7:
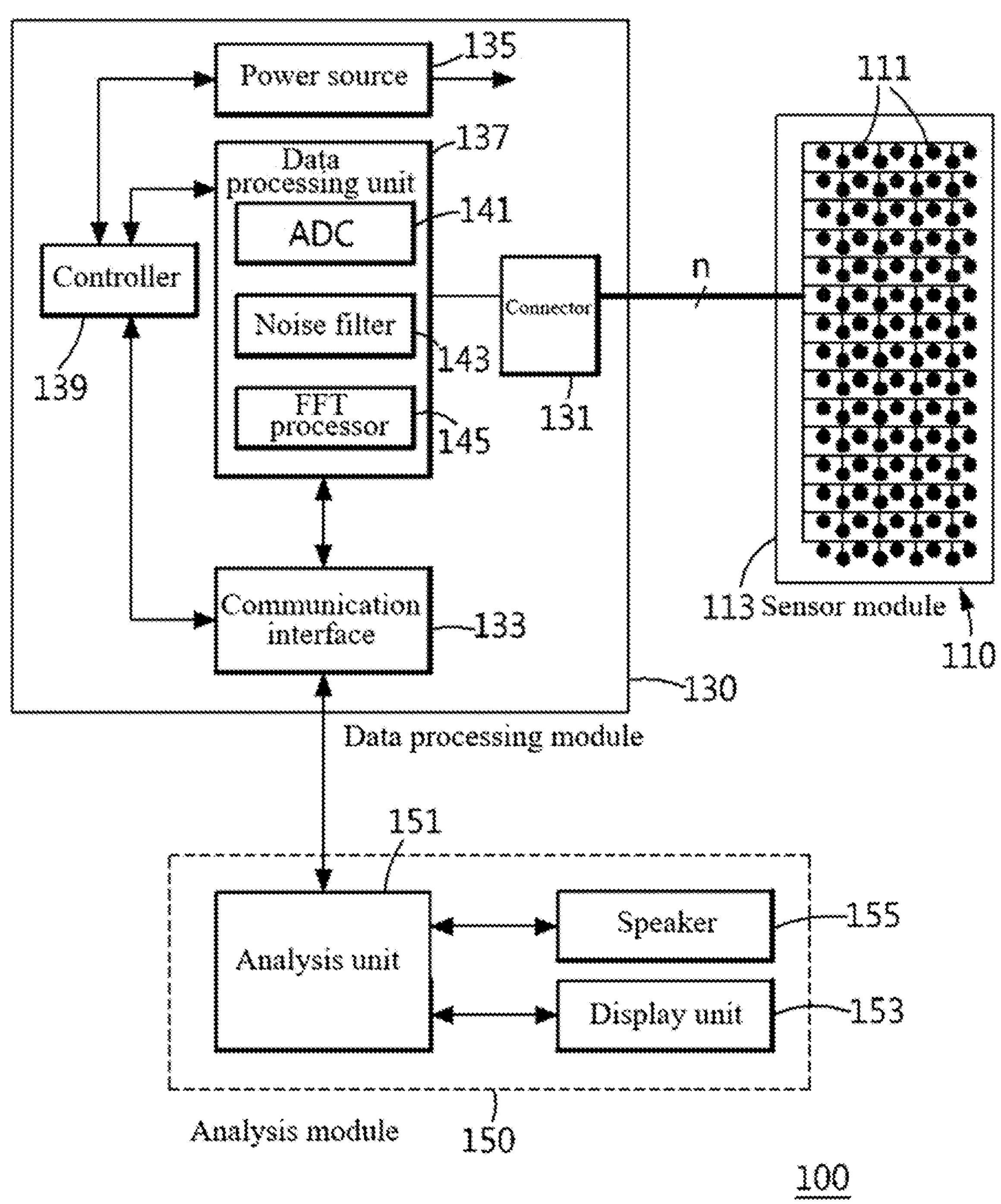
FIG. 7 is a block diagram of a body scanning device according to the present invention.
Figure 8:
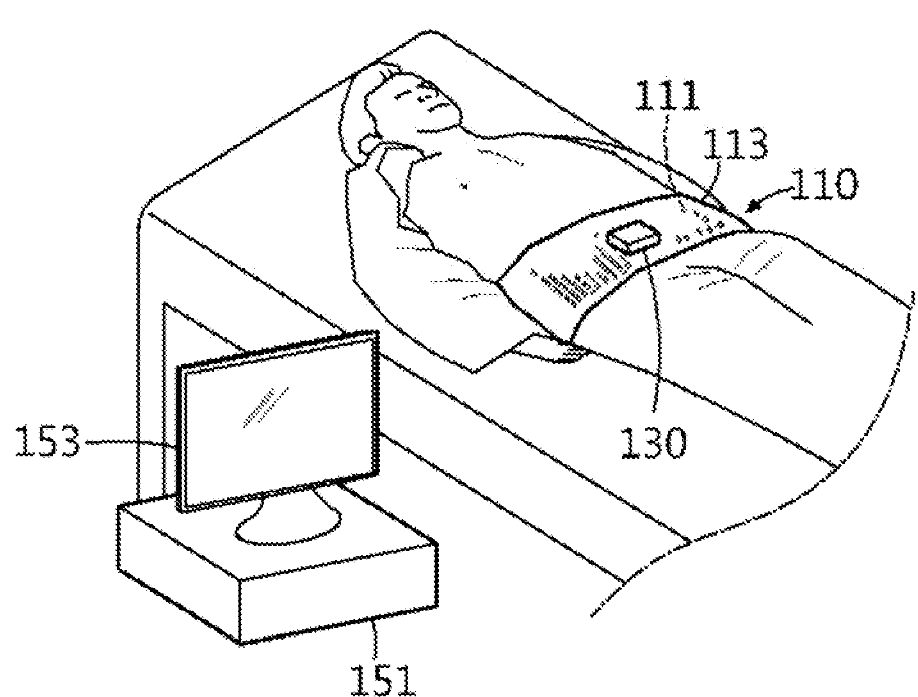
FIG. 8 is a view of one example of the body scanning device according to the present invention.

Referring to FIG. 7 and FIG. 8, a body scanning device 100 according to the present invention includes a sensor module 110 attached to the body of a patient (the chest, the abdomen, and the like), a data processing module 130, and an analysis module 150 to detect a sound generated from the patient body (the lungs, the small intestine, the bronchial tubes, and the like) (hereinafter referred to as "internal body sound") and to recognize a "sound generating location". The data processing module 130 may be realized by a separate component from the sensor module 110 attached to the patient body (the chest, the abdomen, and the like) and may be integrally formed therewith, as shown in FIG. 8. In another embodiment, the data processing module 130 and the analysis module 150 may be realized by one device, such as a kiosk, and the sensor module 110 may be connected to the kiosk.

In another embodiment, the analysis module 150 may be connected to a server through a separate network. The server (not shown) may serve to store and manage analysis results sent from an analysis unit 151 described below or may serve to perform the functions of the analysis unit 151 instead of the analysis unit 151 based on the analysis results of the digital audio signal and the frequency information sent from the analysis module 150.

The sensor module 110 includes multiple microphones 111 attached to the patient body (the chest, the abdomen, and the like) to detect sounds generated from the patient body (the lungs, the small intestine, the bronchial tubes, and the like), an attachment pad 113 receiving the multiple microphones 111, and a soundproof pad (not shown) for sound collection. The sensor module 110 receives operation power supplied from the data processing module 130 and analog audio signals collected by the multiple microphones 111 are supplied to the data processing module 130.

First, the attachment pad 113 receives the multiple microphones 111 to be separated from each other and is attached to the patient abdomen. Accordingly, the attachment pad 113 may be formed of a deformable material, such as a synthetic resin, fibers, a silicone resin, and the like. As shown in FIG. 8, the attachment pad 113 may be realized by a single pad capable of receiving all of the microphones 111 or may be realized by three or four pads separated from each other and each receiving the microphones 111.

The soundproof pad serves to collect sounds generated from the patient abdomen. Accordingly, the soundproof pad has a cylindrical shape and is coupled to an inner surface of the attachment pad 113 with a central axis of the cylindrical shape disposed coincident with a central axis of the attachment pad 113. In addition, the soundproof pad may be formed with multiple grooves (not shown) on an outer surface thereof to secure soundproofing against external noise.

According to the present invention, since the location of a microphone recognizing an internal body sound is treated as a location at which the internal body sound is generated, the microphones 111 may be unidirectional microphones having good sensitivity to sounds in one direction and may have as narrow a sound receiving region as possible. In consideration of a structure where the sensor module 110 is attached to the patient abdomen as shown in FIG. 8, the microphones 111 may be arranged to detect sounds in a direction perpendicular to the attachment pad 113. Furthermore, in order to prevent external noise from being collected by the microphones 111 as much as possible, the microphones 111 may be received in the attachment pad 113 such that a sound collecting surface of each of the microphones 111 can be attached to the patient abdomen.

The microphones 111 may collect sounds both in an audible band and in an inaudible band, preferably audible signals in an audible band of 2 Hz to 2 kHz and in an inaudible band 2 kHz to 80 kHz.

According to the present invention, since the location of the microphone 111 recognizing the internal body sound is treated as a location at which the internal body sound is generated, the sensor module 113 is provided with a number of microphones 111 so as to cover a body scanning region or a target body range. Accordingly, the individual microphones 111 will be referred to as "scan cell" for convenience of description.

For example, for diagnosis of adhesion intestinal stenosis or intestinal adhesion, the microphones 111 are attached to multiple sites in an abdominal region of the patient or in an intestinal region narrower than the abdominal region and are disposed in consideration of the thickness of the small intestine and a general location of the small intestine in the abdomen. In addition, for diagnosis of the lung, arrangement and locations of the microphones 111 may be changed corresponding thereto. Accordingly, the sensor module 110 may have a different size or a different number of microphones 111 depending upon the location thereof.

Since the small intestine is a relatively narrow and fairly long digestive canal that remains clumped rather than stretched out, the scan cells, that is, the microphones 111, may be disposed in a denser arrangement. It is desirable that the microphones 111 be arranged at an interval that allows at least 8 microphones 111 to detect the internal body sound generated from one site. In consideration of these circumstances, the sensor module 110 may be provided with dozens of microphones 111. Referring to FIG. 7 and FIG. 8, by way of example, the multiple microphones 111 are arranged at constant intervals in a two-dimensional matrix so as to cover the abdomen (or a small intestinal region) of a patient. It should be understood that the multiple microphones 111 may be arranged at different intervals depending on arrangement of the small intestine obtained through experiments or statistics.

The sensor module 110 detects the sounds generated from the patient abdomen and supplies data of the sounds to the data processing module 130. If necessary, it may be desirable to collect sound after the patient performs a preset artificial motion. For example, it is desirable that the sensor module 110 detect the body internal sound produced from the patient body when food (or digested food) passes through the digestive canal after the patient has swallowed the food for diagnosis of intestinal stenosis and the like. Although the sensor module 110 is attached to the patient abdomen and each of the microphones 111 is unidirectional, external noise other than abdominal sounds can be collected together with sounds from organs other than the digestive canal.

The multiple microphones 111 received in the attachment pad 113 may be attached to or brought into close contact with multiple sites separated from each other on the patient abdomen.

The data processing module 130 supplies operation power to the sensor module 110 and converts the internal body sound detected by the sensor module 110 into digital signals to supply the digital signals to the analysis module 150. To this end, the data processing module 130 includes a connector 131, a communication interface 133, a power source 135, a data processing unit 137, and a controller 139. For implementation of hardware of the data processing module 130, the data processing unit 137 and the controller 139 may be implemented as separate dedicated chips, or may be implemented by combining an audio IC, a DSP chip, an MCU, and the like.

The power source 135 supplies operation power not only to the data processing module 130 but also to the sensor module 110. For power supply to the multiple microphones 111, an output terminal of the power source 135 is directly connected to each of the microphones 111 through series and/or parallel connection. In the embodiment shown in FIG. 9 described below, the power source 135 may also supply electric power for turning on a marking lamp 311.

The connector 131 supplies the analog audio signals collected by the multiple microphones 111 to the data processing unit 137. The analog audio signals collected by the multiple microphones 111 are supplied to the data processing unit 137 through individual channels to be distinguished from each other. However, since it is difficult for a general data processing unit 137 to have several dozen channels (or input terminals), the connector 131 supplies the analog audio signals collected by the multiple microphones 111 to the data processing unit 137 after muxing the analog audio signals, and the data processing unit 137 classifies the analog audio signals into audio signals of individual channels through demuxing of the analog audio signals. Accordingly, the data processing unit 137 including several dozen channels (or input terminals) may omit the connector 131.

The communication interface 133 is a communication means for connection between the data processing unit 137 to the analysis unit 151 and supplies digital audio signals of multiple channels obtained by the data processing unit 130 and frequency information of the digital audio signal (FFT results) to the analysis module 150. The communication interface 133 is used when the data processing module 130 is realized as a separate device from the analysis unit 151. Accordingly, the communication interface 133 is not essential to the present invention and may be omitted when the data processing module 130 is integrally formed with the analysis unit 151. The communication interface 133 may be a wired interface or may be a wireless interface as shown in FIG. 8.

The data processing unit 137 converts the audio signal of each channel input through the connector 131 into a digital signal to supply the digital signal to the analysis unit 151. The data processing unit 137 may perform fundamental noise filtering to remove white noise or noise less than a predetermined level.

The data processing unit 137 includes an ADC 141, a noise filter 143 and an FFT processor 145.

The ADC 141 converts the analog audio signal supplied from each of the microphones 111 through the connector 131 through sampling and quantization of the analog audio signals. When the microphones 111 have a bandwidth of up to 80 kHz, a sampling frequency is set to about two times of the bandwidth, that is, about 160 kHz or more, according to the Nyquist theorem. The noise filter 143 removes primary noise, such as white noise and the like, from the converted digital signal.

The FFT processor 145 extracts frequency information of the audio signal for each scan cell through fast Fourier transform (FFT) for frequency spectrum analysis of the digital audio signal of each channel.

The controller 139 controls the overall operation of the data processing module 130 and may be typically implemented by an MCU. The controller performs collection of analog signals, conversion of the analog signals into digital signals, and data provision to the analysis module 150 for scanning of the present invention according to request of the analysis module 150.

Figure 9:
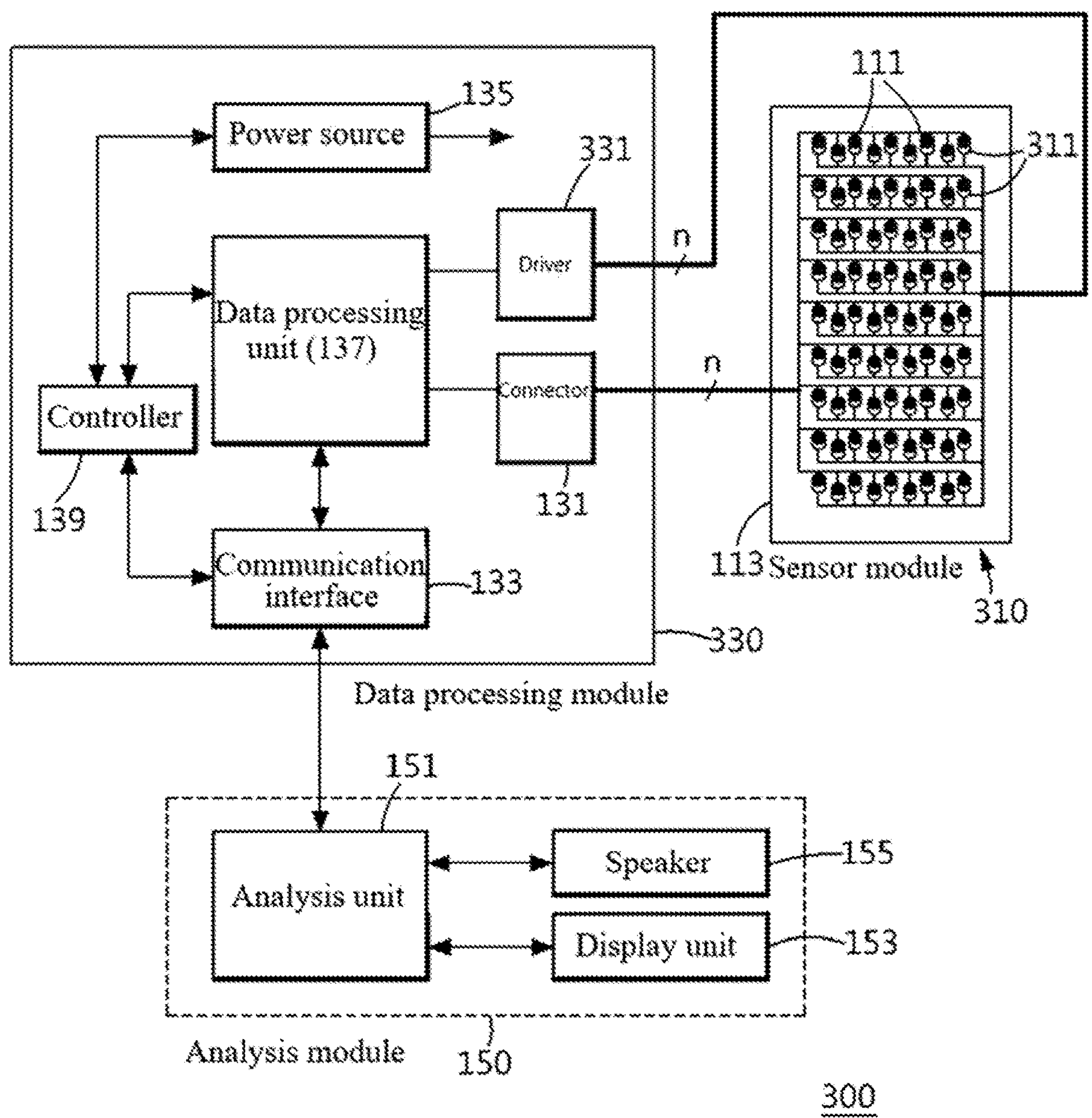
FIG. 9 is a block diagram of a body scanning device according to another embodiment of the present invention.

Referring to FIG. 7 and FIG. 9, the analysis module 150 is separated from the data processing module 130 and is connected thereto through a communication channel. Alternatively, as described above, the analysis module 150 may be integrally formed with the data processing module 130.

The analysis module 150 may locate the internal body sound based on the digital audio signal sent from the data processing module 130 and mark a location at which the internal body sound is generated. To this end, the analysis module 150 includes the analysis unit 151 and the display unit 153. Next, operation of the analysis unit 151 according to the present invention will be described with reference to FIG. 7 to FIG. 11.

<Sound Collection: S501>

The sensor module 110 collects sounds generated from the abdomen of a patient through the multiple microphones 111 and the data processing unit 137 converts audio signals supplied through the multiple channels into digital signals and obtains frequency information through fast Fourier transform (FFT) of the digital signals. The digital audio signal of each channel obtained by the data processing unit 137 and the frequency information thereof are supplied to the analysis unit 151. This process is performed under control of the controller 139, which may receive a control command directly from a user or from the analysis module 150.

<Classification and Location of Internal Body Sound: S503, S505>

The analysis unit 151 classifies an internal body sound among digital audio signals supplied from the data processing unit 137 through multiple channels (that is, multiple microphones). The sounds collected by the sensor module 110 may include not only the internal body sound but also various types of noise. In some cases, only noise can be collected without the internal body sound.

Detailed classification of the internal body sound by the analysis unit 151 may be realized by various algorithms. For example, (1) the analysis unit 151 may classify all sounds having a predetermined level or more into the internal body sound. Since the body scanning device 100 according to the present invention is an assistant device for diagnosis of intestinal stenosis or lung cancer and final diagnosis relies on doctors or medical professionals, it may be necessary to recognize and mark the location of all sounds having a predetermined level or more.

(2) In another example, the analysis unit 151 may analyze the frequency information provided by the data processing module 130 using artificial intelligence. To this end, the analysis unit 151 is provided with an artificial intelligence algorithm or engine and learns the frequency characteristics of the internal body sound traced by the scanning device 100 according to the present invention. It is desirable that the analysis unit learn frequency characteristics of a sound generated when the internal organs of the patient have a medical problem (hereinafter referred to as "sound of interest") among the internal body sounds. For example, the analysis unit learns the characteristics of sounds associated with intestinal stenosis or intestinal adhesion, alveolar sounds associated with lung cancer, or bronchial sounds associated with asthma.

With the artificial intelligence algorithm, the analysis unit 151 may classify an audio signal having similar or the same characteristics as the frequency information as the sound of interest through analysis of the frequency information supplied from the data processing module 130 and may classify an audio signal not having similar or the same characteristics as the frequency information as noise.

When there is an internal body sound among the audio signals supplied from the data processing unit 137 through the multiple channels, the analysis unit 151 may recognize a location at which a signal classified as the corresponding internal body sound is collected, (that is, a location of the corresponding microphone), as a location at which the internal body sound is generated.

<Marking Location of Internal Body Sound: S507>

The analysis unit 151 may inform a manager or a patient of the location at which the audio signal classified as the internal body sound is collected by marking the location. Here, the analysis module 150 may mark the location in various ways. First, the analysis unit 151 marks the location at which the internal body sound is generated.

For example, by tracing the internal body sound after the patient has swallowed food, it is possible to trace a region of the digestive canal through which the food is passing. If there are regions in which intestinal stenosis or intestinal adhesion occurs, it is marked that movement of the food is no longer progressing. Accordingly, if the internal body sound progresses and then stops, a doctor can suspect that intestinal twisting, intestinal bending, intestinal stenosis, or intestinal adhesion occurs in the corresponding region. Even in the case of lung cancer, if a specific part of the lung has an abnormality, a minute sound generated in the corresponding part during the respiration process may be located.

Figure 10:
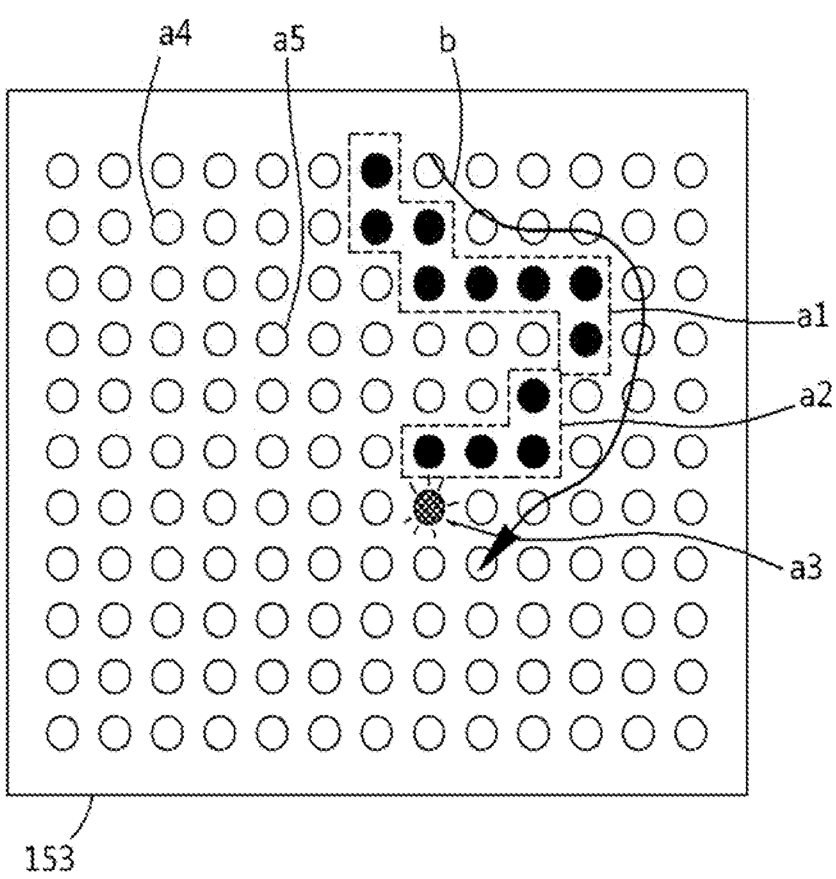
FIG. 10 is a view of one example of an internal body sound detection map displayed on a display unit.
Figure 11:
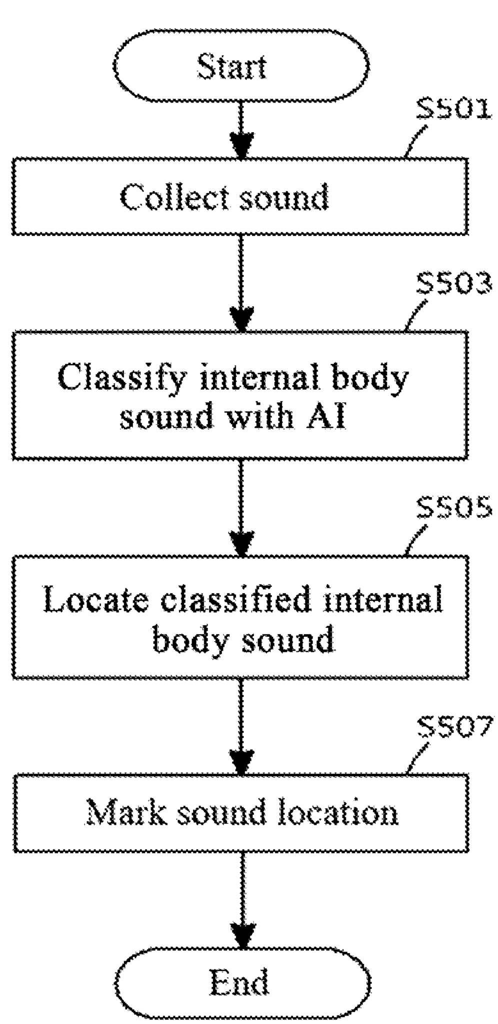
FIG. 11 is a flowchart illustrating operation of the body scanning device according to the present invention.

Therefore, the analysis module 150 marks the location where the signal classified as the internal body sound is collected, that is, the location where the internal body sound is generated. To this end, as shown in FIG. 7 to FIG. 9, the analysis module 150 may be provided with a display unit 153. The display unit 153 is a typical display device, such as a liquid crystal display (LCD), a light emitting diode (LED) display, an organic light emitting diode (OLED) display, a Braun tube, and the like. The analysis unit 151 may display a matrix map or a lattice map on the display unit 153, as shown in FIG. 10. FIG. 10 shows one example of a screen displayed on the display unit 153 upon scanning of the digestive canal. Marks a1, a2, a3, a4, a5 corresponding to the multiple microphones 111 of the sensor module 110 are marked at intersection points on the matrix map. In other words, each of the marks a1, a2, a3, a4, a5 corresponds to the scan cell. The analysis unit 151 marks the locations of the microphones 111 detecting the internal body sounds on a two-dimensional lattice map. Referring to FIG. 10, twelve marks a1, a2 are marked in a turned on state and a thirteenth mark a3 is marked in a turned off state to indicate that the last internal body sound is obtained at the location of the thirteenth mark a3. Accordingly, the doctor can confirm that food is moving in an arrow direction. For scanning of the digestive canal, the internal body sound captured at another location, for example, at a4 or a5, which is not included in the series of connected flows, may be classified as noise.

FIG. 9 is a block diagram of a body scanning device 300 according to another embodiment of the present invention. The scanning device 300 shown in FIG. 9 has the same configuration as the scanning device 100 shown in FIG. 7, except that a sensor module 310 further includes multiple marking lamps 311 together with the multiple microphones 111 and a data processing module 330 further includes a drive unit 331 for driving the marking lamps 311. The power source 135 supplies power to the marking lamps 311.

The marking lamps 311 are attached to the multiple microphones 111 mounted on a scanning module 310, respectively. Under control of the analysis unit 151, the drive unit 331 turns on the marking lamp 311 attached to the microphone 111 that detects the internal body sound, whereby a current location of the internal body sound can be directly marked on the patient. Since the location marked on the display unit 153 does not indicate a particular location inside the patient body, the location marked on the display unit 153 may be marked on the patient through the marking lamp 311. The marking lamps 311 may be realized by LEDs or other lamps similar thereto.

The drive unit 331 is a switch block connecting the power source 135 to the multiple marking lamps 311 and individually controls supply of operation power to the multiple marking lamps 311. Here, the drive unit 331 may open a particular switch in response to a separate control signal to allow a particular marking lamp 311 to be turned on. When the analysis unit 151 recognizes the location at which the internal body sound is detected, the analysis unit 151 informs the drive unit 331 of the corresponding location through the data processing unit 137.

According to this embodiment, the body scanning device 300 may further include a speaker 155 that outputs the detected internal body sound under control of the analysis unit 151. An experienced doctor can determine whether the sound output from the speaker 155 is the internal body sound.

The body scanning device according to the present invention is operated by the method described above.

Example 1

Figure 12:
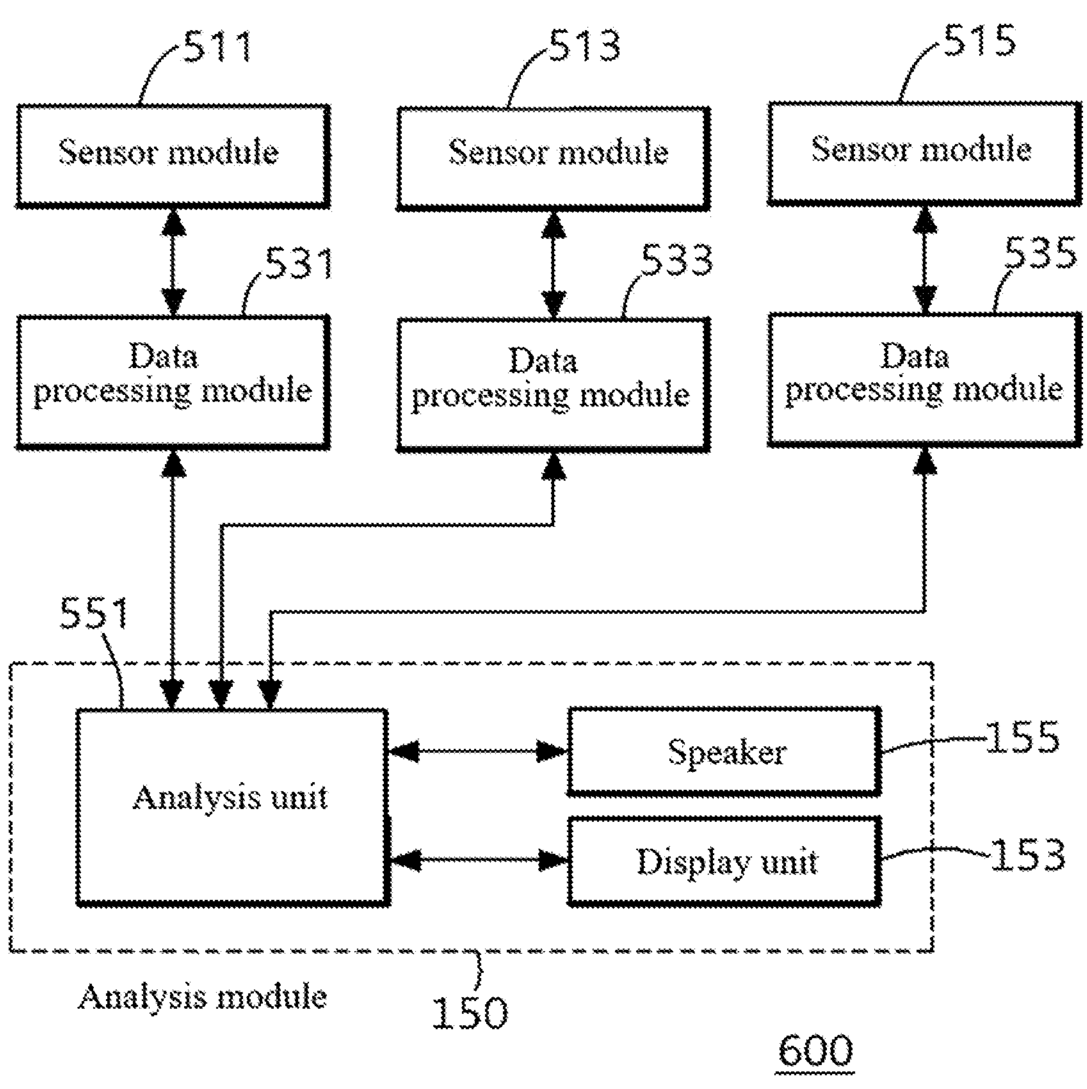
FIG. 12 is a block diagram of a body scanning device according to a further embodiment of the present invention.

FIG. 7 and FIG. 9 show one example in which one data processing module 130 and the sensor module 110 are connected to the analysis module 150. In another embodiment, multiple data processing modules may be connected to the analysis module 150. FIG. 12 shows a scanning device 600 in which an analysis module 150 is connected to multiple data processing units 531, 533, 535, which are connected to sensor modules 511, 513, 515, respectively. Connection between the multiple data processing units 531, 533, 535 and the sensor modules 511, 513, 515 is not limited to a particular structure so long as the multiple data processing units 531, 533, 535 and the sensor modules 511, 513, 515 can be used for scanning of one patient.

The sensor modules 511, 513, 515 are one example of the sensor module 110 realized using multiple pads, as described in the embodiments of FIG. 7 and FIG. 9. Accordingly, the configuration and operation of the sensor modules are the same as the sensor module 110. In this embodiment, each of the sensor modules 511, 513, 515 includes a smaller number of microphones 111 than the sensor module 110 shown in FIG. 7 and FIG. 9.

The data processing units 531, 533, 535 distribute the role of the data processing unit 130 shown in FIG. 7 and FIG. 9. Although each of the data processing units 531, 533, 535 has the same inner configuration as the data processing unit 130, each of the data processing units 531, 533, 535 has a smaller number of treatment audio channels than the data processing unit 130. Accordingly, the data processing units 531, 533, 535 may omit the connector 131.

An analysis unit 551 is connected to the multiple data processing units 531, 533, 535 and the methods of classifying the internal body sound and marking the sound generating location are the same as those of the analysis unit 551 shown in FIG. 7 and FIG. 9.

Example 2

In the process of locating the sound in S503, sound location through artificial intelligence is described. Analysis (learning) through artificial intelligence includes (1) a process of learning characteristics of the internal body sound and may further include (2) a process of learning a pattern of collecting the internal body sound between the multiple scan cells of the sensor module 113. Furthermore, the learning processes (1) and (2) may be restricted to a sound of interest capable of assisting in clinical diagnosis of patient disease. Since the scanning devices 100, 300, 600 according to the present invention uses the sound in the audible and inaudible bands, the scanning devices 100, 300, 600 are particularly conducive to diagnosis of disease that is not difficult to diagnose using a conventional body scanning device, such as computed tomography (CT) or magnetic resonance imaging (MM).

<Learning of Characteristics of Internal Body Sound>

In this process, frequency characteristics of sounds generated from the internal body are learned among various sounds generated from the patient body. Since such learning is aimed at learning frequency characteristics of the corresponding sound, it is premised that the AI algorithm or the AI engine obtains frequency information through fast Fourier transform (FFT) of audio signals provided as learning data.

<Pattern of Collecting Internal Body Sound Between Scan Cells>

The sensor module 113 includes the multiple microphones 111, each of which acts as a scan cell. In other words, a location of each scan cell is a very important factor in operation of the scanning devices 100, 300, 600 according to the present invention. The internal body sounds may be transmitted in various directions depending on the size of the body tissue producing the sounds, the magnitude of the sounds produced therefrom, and the type and shapes of media that transmit the sounds, and a transmission range and collecting time of the sounds may also be changed. Depending on arrangement and complexity of the scan cells, the multiple scan cells may collect the same sound at the same time or at different times. In summary, the pattern of collecting the internal body sound between the multiple scan cells may also be an important factor to distinguish the internal body sound from noise and the location at which the internal body sound is generated can be recognized more accurately through analysis of the pattern.

For example, since the small intestine is a single connected canal regardless of an arrangement shape of the small intestine in the patient abdomen, sounds generated from the abdomen are captured as a stream by the multiple microphones 111 arranged in a matrix or in an array. Accordingly, an internal body sound not included in a series of streams may be classified as noise. For example, in comparison of locations at which multiple audio signals are generated with each other, an audio signal generated from a location separated a predetermined distance from locations at which other audio signals are generated may be treated as noise.

Based on the learning processes (1) and (2), the analysis units 151, 551 may classify an audio signal having similar or the same characteristics as the frequency information as the internal body sound through analysis of the frequency information supplied from the data processing modules 130, 330, 531, 533, 535 and may classify an audio signal not having similar or the same characteristics as the frequency information as noise.

Next, an acoustic digestive organ monitoring system according to the present invention will be described.

Figure 13:
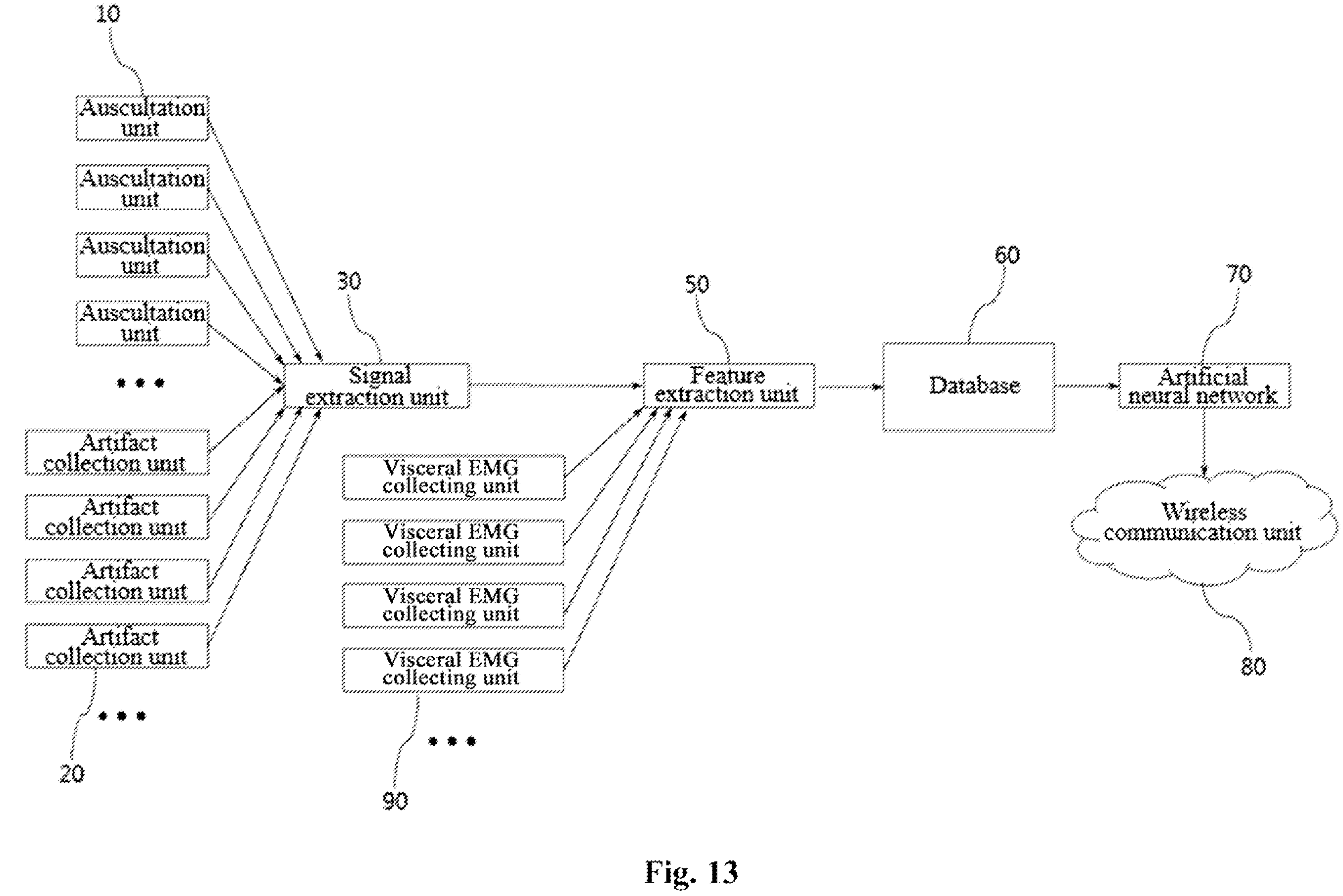
FIG. 13 is a block diagram of an acoustic digestive organ monitoring system according to the present invention.

Referring to FIG. 13, the acoustic digestive organ monitoring system according to the present invention includes an auscultation unit 10, an artifact collection unit 20, a signal extraction unit 30, a feature extraction unit 50, a database 60, an artificial neural network 70, and a wireless communication unit 80.

The auscultation unit 10 is provided in plural to be attached to various sites on the abdomen of a patient and collects a biological sound group generated from the patient digestive system. Here, the biological sound group means various sounds generated from the patient digestive system.

The auscultation unit 10 includes multiple microphones collecting the biological sounds and a health belt on which the multiple microphones are arranged to be attached to the patient abdomen.

In addition, the auscultation unit 10 may include attachment members provided with the microphones and attached to various sites on the patient abdomen.

The attachment member may be formed of an attachment sheet or film capable of being attached to the patient skin.

The microphones may have an audible band of 20 Hz to 20,000 Hz.

The artifact collection unit 20 is provided singularly or in plural to be attached to the patient abdomen to collect an artifact group generated outside the patient. Here, the artifact group means sounds generated from patient breathing, heartbeat, patient movement, patient vocalization, and the like.

The signal extraction unit 30 removes the artifact group from the biological sound group by comparing the biological sound group collected by the auscultation unit 10 with the artifact group collected by the artifact collection unit 20.

More specifically, the auscultation unit 10 collects not only the biological sound group generated from the patient digestive system but also the artifact group, such as sounds generated due to patient breathing, heartbeat, patient movement, patient vocalization, and the like. Thus, the artifact collection unit 20 collects only the artifact group and the signal extraction unit 30 removes the artifact group from the biological sound, thereby enabling extraction of only the sounds of the digestive system from the biological sound group.

The signal extraction unit 30 filters noise from the biological sound group, from which the artifact group is removed.

The feature extraction unit 50 extracts multiple biological sound sources from the biological sound group through division of the biological sound group, from which noise is filtered by the signal extraction unit 30, into the multiple biological sound sources based on spatial features of the patient digestive system.

Here, since the spatial features of the digestive system refer to each point in the patient digestive system and the biological sound group is an aggregation of multiple biological sound sources collected by the auscultation units 10 at each point in the patient digestive system, it is necessary to divide the biological sound group into multiple biological sound sources generated at each point in the patient digestive system.

That is, many biological sound sources show different frequency characteristics, such as frequency bands and periods. For example, the biological sound source of the stomach may have frequency characteristics in a low frequency band and the biological sound source of the large intestine may have frequency characteristics in a higher frequency band than the biological sound source of the stomach.

The database 60 receives the biological sources extracted by and input from the feature extraction unit 50.

The artificial neural network 70 continuously monitors the biological sources input to the database 60 and outputs a biological sound target corresponding to a digestive system disease as a diagnosis result among the biological sound sources input to the database 60.

Here, the artificial neural network 70 may learn the spatial features of the patient digestive system and a weight of a predetermined biological sound target through machine learning of the biological sources input to the database 60 as learning data.

In addition, the artificial neural network 70 may perform learning by matching the biological sound group collected by the auscultation unit 10 with the multiple biological sound sources extracted by the feature extraction unit 50.

Further, the artificial neural network 70 may include a built-in digital signal processor (DSP) that converts analog signals of the biological sources input to the database 60 into digital signals.

The wireless communication unit 80 sends the diagnosis result of the artificial neural network to a control server.

Thus, the acoustic digestive organ monitoring system accordingly to the present invention advantageously enables early diagnosis of disease in the patient digestive system by continuously monitoring the patient digestive system through establishment of the database 60 based on the biological sounds generated from the digestive system.

The acoustic digestive organ monitoring system may further include multiple visceral electromyography (EMG) collecting units 90 each collecting motion potentials of the visceral muscles generated in the internal organs as a visceral EMG group and transmitting the visceral EMG groups to the feature extraction unit 50.

More specifically, the EMG collecting units 90 may collect the motion potentials of the visceral muscles (action potentials at one visceral point), which are measured by inserting a needle electrode into a point close to the internal organs or by attaching a skin electrode to one point of the patient skin close to the internal organs, as a visceral EMG group.

In addition, signal processing of the visceral EMG group collected by the EMG collecting units 90 is performed as follows.

First, the visceral EMG group collected by the EMG collecting units 90 is sent to the feature extraction unit 50.

Next, the feature extraction unit 50 divides and extracts the visceral EMG group into multiple visceral EMG sources using the spatial features of the patient internal organs. Here, the spatial features mean that the frequency characteristics are different for each part of the patient internal organs.

Next, the visceral EMG sources are input to the database 60.

Next, the artificial neural network 70 monitors the visceral EMG sources input to the database 60 and outputs a visceral EMG target corresponding to a digestive system disease as a diagnosis result among the visceral EMG sources.

Next, the wireless communication unit 80 sends the diagnosis result of the artificial neural network to the control server.

The above embodiments may be implemented as a hardware component, a software component, and/or combination of hardware components and software components. The apparatus, method and components described in the embodiments may be, for example, a processor, a controller, an arithmetic logic unit (ALU), a digital signal processor, a microcomputer, a field programmable gate array (FPGA), programmable logic (PLU), a microprocessor, and the like, or may be implemented using one or more general purpose or special purpose computers like other devices capable of executing and responding to instructions. The processing device may execute an operating system (OS) and one or more software applications running on the operating system. The processing device may also access, store, manipulate, process, and generate data in response to execution of the software. For convenience of understanding, one processing device may be described as being used. However, it will be understood by a person having ordinary knowledge in the art that the processing device may include a plurality of processing elements and/or a plurality of types of processing elements. For example, the processing device may include a plurality of processors or one processor and one controller. In addition, other processing configurations, such as parallel processors, may be used.

We claim:

1. A body scanning device comprising:

a sensor module comprising multiple microphones attached to multiple sites separated from each other on a patient body to collect an internal body sound from the patient body;

a data processing unit converting audio signals collected by the multiple microphones into digital signals and obtaining frequency information of the audio signals through fast Fourier transform; and an analysis unit classifying the internal body sound generated from the patient body among multiple audio signals generated from the multiple microphones based on the frequency information provided by the data processing unit and recognizing that a location of a microphone detecting the internal body sound is a location at which the internal body sound is generated, wherein the analysis unit learns frequency characteristics of a sound generated from the patient internal organs in a preset state through artificial intelligence to detect an audio signal having the frequency characteristics among audio signals classified as the internal body sound, wherein the multiple microphones are arranged at constant intervals in a two-dimensional matrix, and wherein marking lamps are attached to the multiple microphones, the marking lamp that detects the internal body sound being turned on.

2. The body scanning device according to claim 1, wherein the analysis unit obtains the preset frequency characteristics by learning frequency characteristics of the internal body sound based on frequency information obtained through fast Fourier transform of the multiple audio signals provided as learning data.

3. The body scanning device according to claim 1, wherein the analysis unit locates a part of the patient body generating the internal body sound through analysis of a pattern of collecting the same internal body sounds between the multiple microphones using artificial intelligence.

4. The body scanning device according to claim 1, wherein the sensor module comprises: multiple unidirectional microphones; and an attachment pad attached to the patient abdomen and receiving the multiple microphones to be separated from each other.

5. The body scanning device according to claim 4, wherein the sensor module further comprises a soundproof pad coupled to an inner surface of the attachment pad.

6. The body scanning device according to claim 1, wherein the analysis unit extracts locations, at which the multiple audio signals are generated, and treats an audio signal generated from a location separated a predetermined distance from locations at which other audio signals are generated, as noise.

7. A body scanning method of a body scanning device comprising:

attaching multiple microphones to a scanning target region on a patient body to be separated from each other on the patient body, followed by collecting internal body sounds of the patient body;

converting, by a data processing unit, audio signals collected by the multiple microphones into digital signals to obtain frequency information of the audio signals through fast Fourier transform of the audio signals; and classifying, by an analysis unit, an internal body sound among the audio signals generated from the multiple microphones using the frequency information to recognize that a location of a microphone detecting the internal body sound is a location at which the internal body sound is generated, wherein classifying the internal body sound comprises learning frequency characteristics of a sound generated from the patient internal organs in a preset state through an artificial intelligence algorithm and detecting an audio signal having the frequency characteristics among audio signals classified as the internal body sound by the artificial intelligence algorithm, wherein the multiple microphones are arranged at constant intervals in a two-dimensional matrix, wherein marking lamps are attached to the multiple microphones, the marking lamp that detects the internal body sound being turned on.

8. The body scanning method according to claim 7, wherein classifying the internal body sound comprises obtaining the preset frequency characteristics by learning frequency characteristics of the internal body sound based on frequency information obtained through fast Fourier transform of the multiple audio signals provided as learning data.

9. The body scanning method according to claim 7, wherein classifying the internal body sound comprises locating, by an artificial intelligence algorithm, a part of the patient body generating the internal body sound through analysis of a pattern of collecting the same internal body sounds between the multiple microphones using the artificial intelligence algorithm.

* * * * *